United States Patent
Lee

(10) Patent No.: US 12,097,308 B2
(45) Date of Patent: Sep. 24, 2024

(54) BIO-ELECTRODE FOR MEASURING BIO-SIGNAL AND PRODUCING ELECTRICAL ACTIVITY BASED ON NANO-POROUS PERMEABLE MEMBRANE HAVING HIGH SPECIFIC SURFACE AREA AND METHOD OF MANUFACTURING THE SAME

(71) Applicant: KNU—Industry Cooperation Foundation, Gangwon-Do (KR)

(72) Inventor: Kwang Ho Lee, Gangwon-Do (KR)

(73) Assignee: KNU-Industry Cooperation Foundation, Gangwon-do (KR)

( * ) Notice: Subject to any disclaimer, the term of this patent is extended or adjusted under 35 U.S.C. 154(b) by 1277 days.

(21) Appl. No.: 16/642,822

(22) PCT Filed: Jun. 19, 2018

(86) PCT No.: PCT/KR2018/006891
§ 371 (c)(1),
(2) Date: Feb. 27, 2020

(87) PCT Pub. No.: WO2019/004645
PCT Pub. Date: Jan. 3, 2019

(65) Prior Publication Data
US 2020/0289017 A1    Sep. 17, 2020

(30) Foreign Application Priority Data
Jun. 29, 2017    (KR) .......................... 10-2017-0082367

(51) Int. Cl.
A61L 31/14        (2006.01)
A61B 5/053       (2021.01)
(Continued)

(52) U.S. Cl.
CPC ............ *A61L 31/146* (2013.01); *A61B 5/053* (2013.01); *A61L 31/041* (2013.01); *A61L 31/088* (2013.01);
(Continued)

(58) Field of Classification Search
CPC .... A61L 31/146; A61L 31/041; A61L 31/088; A61L 31/10; A61L 31/14; B33Y 10/00;
(Continued)

(56) References Cited

FOREIGN PATENT DOCUMENTS

KR    10-2008-0012120 A    2/2008
KR    10-2010-0048648 A    5/2010
(Continued)

OTHER PUBLICATIONS

Soltanian, Saeid, et al. "Highly stretchable, sparse, metallized nanofiber webs as thin, transferrable transparent conductors." Advanced Energy Materials 3.10 (2013): 1332-1337. (Year: 2013).*
(Continued)

*Primary Examiner* — Robert J Eom
(74) *Attorney, Agent, or Firm* — Harness, Dickey & Pierce, P.L.C.

(57) ABSTRACT

The present invention relates to a bio-electrode having improved conductivity, flexibility and bio-compatibility, and a method of manufacturing the same. Specifically, the present invention relates to a conductive polymer bio-electrode including nano-porous permeable membrane, based on a bio-compatible polymer material having a plurality of pores and an improved surface area based on a PDMS device having a low mechanical strength and an excellent bio-compatibility, bio-signal transmission patterning, and a gold coating layer and has an excellent bio-compatibility and low rejection response while having a conductivity similar to that of a bio-electrode configured with a metal material of the related art. Therefore, the conductive polymer bio-
(Continued)

electrode of the present invention is expected to be able to replace a bio-electrode configured with a metal material by which the bio-signal transmission efficiency is degraded due to a high bio-incompatibility.

6 Claims, 11 Drawing Sheets

(51) Int. Cl.
  *A61L 31/04*    (2006.01)
  *A61L 31/08*    (2006.01)
  *A61L 31/10*    (2006.01)
  *B29C 64/106*    (2017.01)
  *B33Y 10/00*    (2015.01)
  *B33Y 40/20*    (2020.01)
  *B33Y 70/00*    (2020.01)
  *B33Y 80/00*    (2015.01)
  *C08J 7/04*    (2020.01)
  *C08J 7/044*    (2020.01)
  *D01D 5/00*    (2006.01)
  *B29K 83/00*    (2006.01)
  *B82Y 30/00*    (2011.01)

(52) U.S. Cl.
  CPC .............. *A61L 31/10* (2013.01); *A61L 31/14* (2013.01); *B29C 64/106* (2017.08); *B33Y 10/00* (2014.12); *B33Y 40/20* (2020.01); *B33Y 70/00* (2014.12); *B33Y 80/00* (2014.12); *C08J 7/0423* (2020.01); *C08J 7/044* (2020.01); *D01D 5/003* (2013.01); *A61B 2562/0214* (2013.01); *A61B 2562/125* (2013.01); *A61L 2420/02* (2013.01); *A61L 2420/08* (2013.01); *B29K 2083/00* (2013.01); *B82Y 30/00* (2013.01); *C08J 2383/04* (2013.01); *C08J 2475/04* (2013.01); *D10B 2331/10* (2013.01)

(58) Field of Classification Search
  CPC ......... B33Y 70/00; B33Y 80/00; B33Y 40/00; B29C 64/106; C08J 7/044; A61B 5/053; D01D 5/003
  See application file for complete search history.

(56) References Cited

FOREIGN PATENT DOCUMENTS

KR   10-2014-0082380 A   7/2014
KR   10-1636778 B1   7/2016

OTHER PUBLICATIONS

Lee, Kwang Ho, et al. "Hydrophilic electrospun polyurethane nanofiber matrices for hMSC culture in a microfluidic cell chip." Journal of Biomedical Materials Research Part A: An Official Journal of The Society for Biomaterials, 90.2 (2009): 619-628. (Year: 2009).*

Ostrovidov, Serge, Yasuyuki Sakai, and Teruo Fujii. "Integration of a pump and an electrical sensor into a membrane-based PDMS microbioreactor for cell culture and drug testing." Biomedical microdevices 13 (2011): 847-864. (Year: 2011).*

3D Systems, Inc., "Material Handling and Post Processing Guide." [Online], 2012.

International Search Report dated Oct. 17, 2018, issued in International Patent Application No. PCT/KR2018/006891, with English translation.

* cited by examiner

BIO-ELECTRODE FOR MEASURING BIO-SIGNAL AND PRODUCING ELECTRICAL ACTIVITY BASED ON NANO-POROUS PERMEABLE MEMBRANE HAVING HIGH SPECIFIC SURFACE AREA AND METHOD OF MANUFACTURING THE SAME

CROSS-REFERENCE TO RELATED APPLICATIONS

This application is a national phase application of PCT Application No. PCT/KR2018/006891, filed on Jun. 19, 2018, which claims the benefit and priority of Korean Application No. 10-2017-0082367, filed on Jun. 29, 2017. The entire disclosures of the applications identified in this paragraph are incorporated herein by reference.

FIELD

The present invention relates to a bio-electrode capable of measuring a bio-signal based on a nano-porous permeable membrane having a high specific surface area, and having a variable capacitance, conductivity, flexibility, and bio-compatibility, and a method of manufacturing the same. Specifically, the bio-electrode is a bio-electrode that transmits and receives electrical signals with body organs and is inserted into a living body to perform electrical interaction with cells and has advantages of no rejection response and no immune response due to excellent flexibility and bio-compatibility while having a conductivity similar to that of the metal electrode of the related art.

BACKGROUND

The bio-electrode is an electrode for measuring a signal of a human body and applying a signal, and the bio-electrode is attached to the outside of the body or inserted into the body and is used to exchange electrical signals with organs and tissues of the body and to electrically interact with tissues and cells. Since the bio-electrode performs delicate interactions in a living body environment, the bio-electrode requires a low specific resistance that can mediate minute electrical signals of a living body and an excellent bio-compatibility and a low mechanical strength that can allow for a low rejection response and stable interactions with a living tissue. In the related art, a bio-electrode configured with a metal material has a disadvantage in that an immune response is induced due to bio-incompatibility of the metal being in contact with a living tissue, and thus, the efficiency of the bio-electrode is degraded. The bio-incompatibility of the metal denotes a high mechanical strength and ions released from the metal. The bio-incompatibility of the metal causes immune cells to gather around the inserted bio-electrode and causes an inflammatory response to occur at the interface of the organ or tissue to which the bio-electrode is attached. The inflammatory response interferes with signal transmission between the bio-electrode and the organ or tissue and separates cells from the bio-electrode, so that the specific resistance and noise is increased. In addition, in the related art, metal-based bio-electrodes have mechanical incompatibility according to the movement of the organ or tissue due to a high mechanical strength. The mechanical incompatibility creates a gap between the bio-electrode and the organ or tissue, so that the bio-signal transmission efficiency is degraded. Up to date, such a metal-based bio-electrode has not solved a number of disadvantages, and thus research on the bio-electrode configured with a new material has been actively made.

The patent documents and reference documents mentioned in this specification are incorporated herein by reference to the same extent as if each document was individually and clearly specified by reference.

SUMMARY

Technical Problem

In order to solve the above-described problems, the inventors have endeavored to develop a nano-porous permeable membrane-based variable capacitive bio-electrode having a high specific surface area that can be attached to a living body surface for a long time and implanted in the body for diagnosis and measurement of a bio-signal, and then, the inventors manufactured a conductive polymer bio-electrode by attaching a nano-porous permeable membrane configured with polyurethane having an excellent bio-compatibility to a device (substrate) and including a plurality of nano-pores, performing bio-signal transmission patterning, and after that, performing gold coating. The inventors have experimentally confirmed that the manufactured conductive polymer bio-electrode has a low specific resistance at all positions; due to a high specific surface area secured by stacked nano-fibers, the nano-porous permeable membrane is flexible, has an excellent conductivity, and does not degrade the conductivity even by mechanical deformation; and a metal-based bio-electrode of the related art can be replaced because cell culture is possible due to the excellent bio-compatibility, and the inventors completed the present invention.

Accordingly, an object of the present invention is to provide a conductive polymer bio-electrode including a PDMS device, a nano-porous permeable membrane, bio-signal transmission patterning, and a gold coating layer.

Another object of the present invention is to provide a method of manufacturing the conductive polymer bio-electrode.

Other objects and technical features of the present invention are more specifically disclosed by the following detailed description, claims, and drawings.

Technical Solution

According to one aspect of the present invention, the present invention provides a conductive polymer bio-electrode including: a polydimethylsiloxane (PDMS) device having an intaglio groove to which a nano-porous permeable membrane is to be attached and having a thickness of 250 to 350 μm; the nano-porous permeable membrane having a thickness of 50 to 200 μm which is to be attached to the intaglio groove of the PDMS device; a bio-signal transmission patterning formed on the PDMS device and the nano-porous permeable membrane; and a gold (Au) coating layer which is uniformly formed with a thickness of 0.1 to 10 μm on the PDMS device, the nano-porous permeable membrane, and the bio-signal transmission patterning.

According to one embodiment of the present invention, the nano-porous permeable membrane is a permeable membrane having a thickness of 50 to 200 μm manufactured by electrospinning a bio-compatible polymer material and includes a plurality of pores having a diameter of 0.1 to 10 μm, so that the bio-compatibility is excellent to the extent that cell culture is possible.

According to another embodiment of the present invention, the electrospinning is performed by spinning 4 to 6 ml of the electrospinning solution containing the bio-compatible polymer material under conditions of a voltage of 10 to 20 kV, a spinning rate of 0.05 to 0.3 ml/h, a needle diameter of 20 to 30 G, and a spinning distance of 20 to 40 cm in an atmosphere of a humidity of 20 to 40% and a temperature of 25 to 35° C.

According to another aspect of the present invention, the present invention provides a method for manufacturing a 3D substrate for a PDMS device including: (a) a first step of manufacturing a 3D substrate for a PDMS device including an intaglio groove for attaching a nano-porous permeable membrane; (b) a second step of manufacturing a PDMS device including the intaglio groove for attaching the nano-porous permeable membrane by using the 3D substrate; (c) a third step of manufacturing the nano-porous permeable membrane by using electrospinning; (d) attaching the nano-porous permeable membrane to the intaglio groove formed in the PDMS device by using a PDMS solution; (e) a fifth step of performing bio-signal transmission patterning on the PDMS device to which the nano-porous permeable membrane is attached; and (f) a sixth step of performing gold coating on the PDMS device on which the bio-signal transmission patterning is performed.

Effects of the Invention

The present invention relates to a bio-electrode having improved conductivity, flexibility and bio-compatibility, and a method of manufacturing the same. Specifically, the present invention relates to a conductive polymer bio-electrode including nano-porous permeable membrane, based on a bio-compatible polymer material having a plurality of pores and an improved surface area based on a PDMS device having a low mechanical strength and an excellent bio-compatibility, bio-signal transmission patterning, and a gold coating layer and has an excellent bio-compatibility and low rejection response while having a conductivity similar to that of a bio-electrode configured with a metal material of the related art. Therefore, the conductive polymer bio-electrode of the present invention is expected to be able to replace a bio-electrode configured with a metal material by which the bio-signal transmission efficiency is degraded due to a high bio-incompatibility.

DETAILED DESCRIPTION

Figure 1:
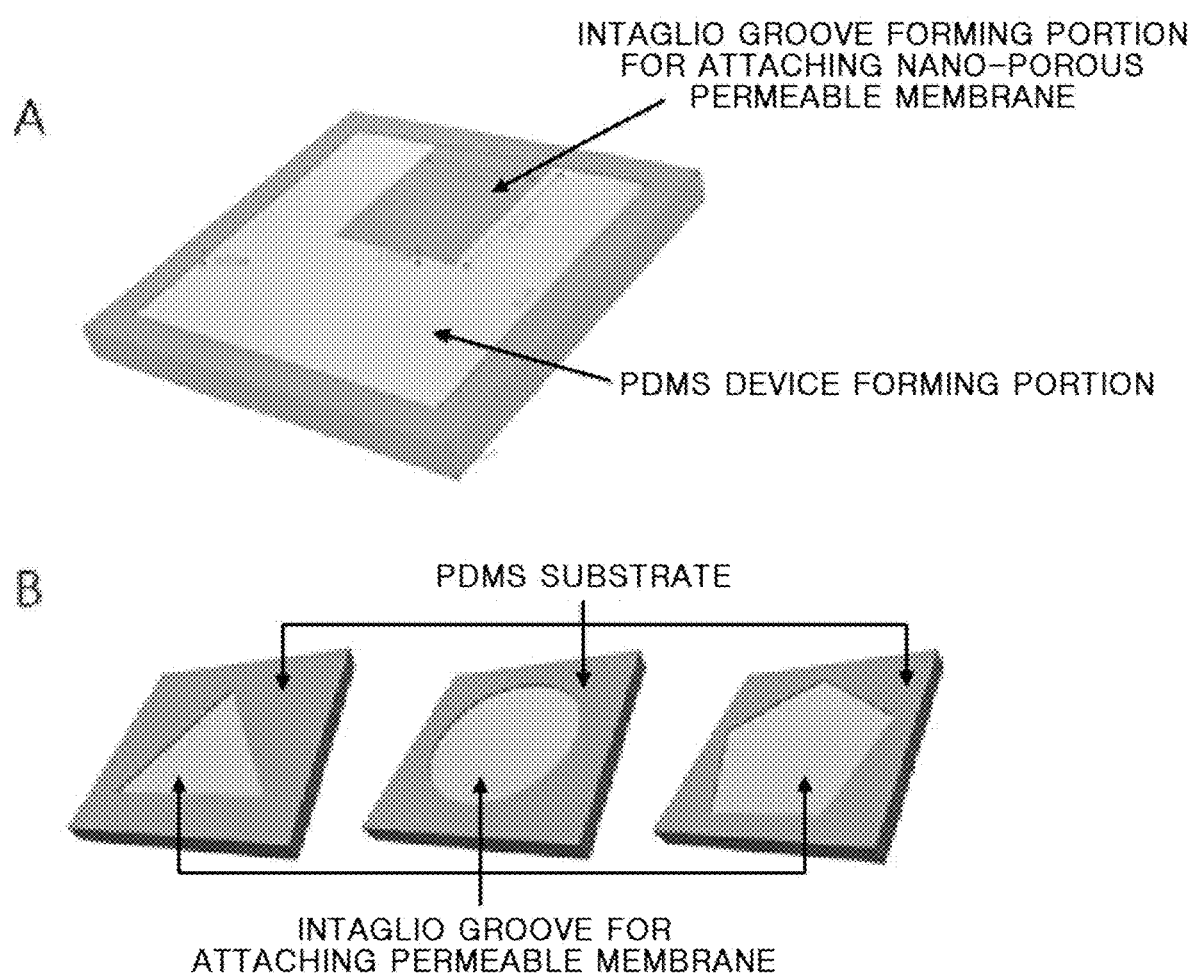
FIG. 1 illustrates a diagram of a 3D substrate for a PDMS device including an intaglio groove for attaching a nano-porous permeable membrane and the PDMS device. Panel A illustrates a diagram of the 3D substrate for the PDMS device including the intaglio groove for attaching a rectangular nano-porous permeable membrane. Panel B illustrates the PDMS device including the intaglio groove for attaching the nano-permeable membrane having various shapes manufactured from the 3D substrate for the PDMS devices.

The present invention provides a conductive polymer bio-electrode including: a polydimethylsiloxane (PDMS) device having an intaglio groove to which a nano-porous permeable membrane is to be attached and having a thickness of 250 to 350 μm; the nano-porous permeable membrane having a thickness of 50 to 200 μm which is to be attached to the intaglio groove of the PDMS device; a bio-signal transmission patterning formed on the PDMS device and the nano-porous permeable membrane; and a gold (Au) coating layer which is uniformly formed with a thickness of 0.1 to 10 μm on the PDMS device, the nano-porous permeable membrane, and the bio-signal transmission patterning.

MODE FOR CARRYING OUT THE INVENTION

According to one aspect of the present invention, the present invention provides a conductive polymer bio-electrode including: a polydimethylsiloxane (PDMS) device having an intaglio groove to which a nano-porous permeable membrane is to be attached and having a thickness of 250 to 350 μm; the nano-porous permeable membrane having a thickness of 50 to 200 μm which is to be attached to the intaglio groove of the PDMS device; a bio-signal transmission patterning formed on the PDMS device and the nano-porous permeable membrane; and a gold (Au) coating layer which is uniformly formed with a thickness of 0.1 to 10 μm on the PDMS device, the nano-porous permeable membrane, and the bio-signal transmission patterning.

The bio-electrode of the present invention denotes an electrode which is inserted into a living body to exchange electrical signals or perform electrical interactions with an organ or tissue. Since the bio-electrode is inserted into the living body, it is preferable that bio-compatibility is high. The degree of bio-compatibility can be determined according to the degree of immunological rejection response that occurs when the bio-electrode is inserted. The immunological rejection response mainly denotes an inflammatory response. Therefore, if the bio-compatibility is excellent, the inflammatory response caused by the insertion of the bio-electrode occurs at a low level. When the inflammatory response occurs, immune cells are gathered around the organ or tissue to which the bio-electrode is attached, and the surrounding cells die by the inflammatory substances secreted from the immune cells to thicken the tissue. When the tissue is thickened, the specific resistance increases, so that the bio-electrical signal cannot be effectively transmitted. The inflammatory response can be caused by various intracellular substances secreted from cell death. Therefore, there is a method of evaluating cytotoxicity of the bio-electrode as a method of determining the bio-compatibility of the bio-electrode. In the present invention, cell culture using the bio-electrode was attempted to evaluate the bio-compatibility of the bio-electrode. The bio-electrode of the present invention includes a nano-porous permeable membrane manufactured by using a polymer material having an excellent bio-compatibility. The permeable membrane contains nano-sized pores, and thus, the cell culture solution can be stored, so that there is an advantage in that the cell culture is possible. The bio-compatibility can be evaluated by comparing the number of living cells with the number of dead cells through staining after the cell culture. In the related art, metal-based bio-electrodes are configured by mainly using platinum, a platinum alloy, or gold. The metal material is good in conductivity but emits excessive metal ions and has a high mechanical strength, so that the metal material induces an inflammatory response. Therefore, there is a disadvantage in that the transmission rate of the bio-signal decreases as the time has elapsed. According to an embodiment of the present invention, the bio-electrode of the present invention is manufactured by using polydimethylsiloxane (PDMS) rather than a metal material. The PDMS is a kind of silicone and is a high molecular material having inert properties, low cost, excellent thermal stability, and bio-compatibility, so the PDMS is widely used in human tissue engineering research. In the bio-electrodes attached inside a living body, mechanical deformation such as bending or bending may occur due to movement of organs and tissues. As described above, a bio-electrode manufactured with a metal material having high mechanical strength may change the attachment degree of the electrode by mechanical deformation, or an inflammatory response (foreign body reaction) caused by a foreign substance may be induced, so that performance as a bio-electrode may be degraded. In contrast, the PDMS of the present invention has the advantage of maintaining the shape without being deformed by an external physical force due to the low mechanical strength and has the advantage of improving a bio-signal transmission efficiency because the PDMS has a good processability, so that the PDMS can be properly processed according to the appearance of the organ or tissue to which attachment is expected. According to one embodiment of the present invention, the PDMS device of the present invention has a thickness of 250 to 350 μm. Preferably, the PDMS device has a thickness of 275 to 325 μm. More preferably, the PDMS device has a thickness of 300 μm. If the thickness is 250 μm or less, the mechanical strength is too weak to manufacture the PDMS device by using the 3D substrate, and thus, is difficult to separate the PDMS device from the 3D substrate. If the thickness exceeds 350 μm, the mechanical strength is increased, and thus, the bio-compatibility is degraded. The PDMS has a low conductivity because the PDMS is a polymer material and is used as an electrode. In the present invention, a PDMS-based bio-electrode having an excellent conductivity while maintaining a high elastic property is manufactured by using a nano-porous permeable membrane configured with nano-fiber bundles and gold (Au) coating. For this purpose, the PDMS device includes an intaglio groove to which the nano-porous permeable membrane can be attached. According to one embodiment of the invention, 25 to 50% of the total area of the PDMS device is an intaglio groove having a depth of 100 to 200 μm for attaching the nano-porous permeable membrane. Since the nano-porous permeable membrane is attached to the intaglio groove, the area of the intaglio groove is the same as that of the nano-porous permeable membrane. If the area of the intaglio groove is less than 25% of the area of the PDMS device, the flexibility improvement effect, the surface area improvement effect and the bio-compatibility improvement effect due to the attachment of the nano-porous permeable membrane are insignificant, and if the area of the intaglio groove exceeds 50% of the area of the PDMS device, the mechanical strength is too low, and thus, the processability of the bio-electrode. The nano-porous permeable membrane can be manufactured as a permeable membrane having nano-sized pores formed by stacking a polymer material having an excellent bio-compatibility in the form of a nano-fiber by using an electrospinning method. It is preferable that the polymer material is a material having a good moldability, a low hardness and mechanical strength, a good chemical resistance, no heat resistance, and an excellent bio-compatibility. According to one embodiment of the invention, the bio-compatible polymer material may be any one or a mixture of two or more selected from a group consisting of polyurethane, polyacetal, polyamide, polyamide elastomer, polyester, polyester elastomer, polystyrene, polypropylene, polyacrylonitrile, polymethylmethacrylate, polyolefin, polysulfone, polyvinyl chloride, silicone, and polyethylene. Preferably, the bio-compatible polymer material is polyurethane. The electrospinning method denotes that the polymer solution having a viscosity is spun instantaneously in the form of a fiber by using an electrostatic force, and by performing the electrospinning, a membrane stacked in the form of a nano-fiber can be manufactured. The membrane may have pores according to the shape of the nano-fibers, and the pores may store bio-active substances, cell-active drugs, or the like, and thus, research on materials of nano drug carriers has been made. According to an embodiment of the present invention, the nano-porous permeable membrane is a permeable membrane having a thickness of 50 to 200 μm manufactured by electrospinning the bio-compatible polymer material and includes a plurality of pores having a diameter of 0.1 to 10 μm. Preferably, the nano-porous permeable membrane is a permeable membrane having a thickness of 100 to 175 μm manufactured by electrospinning the bio-compatible polymer material and includes a plurality of pores having a diameter of 0.1 to 10 μm. More preferably, the nano-porous permeable membrane is a permeable membrane having a thickness of 150 μm manufactured by electrospinning the bio-compatible polymer material and includes a plurality of pores having a diameter of 0.1 to 10 μm. The nano-porous permeable membrane is attached to the intaglio groove of the PDMS device. According to one embodiment of the invention, the intaglio has a depth of 100 to 200 μm. Therefore, when the thickness of the nano-porous permeable membrane is less than 50 μm or exceeds 200 μm, the thickness of the nano-porous permeable membrane does not match the height of the PDMS device, and thus, there is a disadvantage in that uniform gold coating is not possible, so that the bio-signal transmission efficiency is degraded.

According to one embodiment of the invention, the electrospinning is performed by spinning 4 to 6 ml of the electrospinning solution including the bio-compatible polymer 10 to 20 kV, a spinning rate of 0.05 to 0.3 ml/h, a needle diameter of 20 to 20 G, and a spinning distance of 20 to 40 cm and in an atmosphere of a humidity of 20 to 40% and a temperature of 25 to 35° C. Preferably, the electrospinning is performed by spinning 5 ml of the electrospinning solution including the bio-compatible polymer material under conditions of a voltage of 12.5 to 17.5 kV, a spinning rate of 0.075 to 0.2 ml/h, a needle diameter of 22 to 27 G, and a spinning distance of 25 to 35 cm and in an atmosphere of a humidity of 25 to 35% and a temperature of 27.5 to 32.5° C. More preferably, the electrospinning is performed by spinning 5 ml of the electrospinning solution including the bio-compatible polymer material under conditions of a voltage of 15 kV, a spinning rate of 0.1 ml/h, a needle diameter of 25 G, and a spinning distance of 30 cm and in an atmosphere of a humidity of 30% and a temperature of 30° C. If the nano-porous permeable membrane is manufactured out of the conditions of the electrospinning, a permeable membrane having a thickness different from that of the intaglio groove of the PDMS device is manufactured, and thus, the height does not match at the time of attachment to the PDMS device, so that uniform gold coating is not possible. According to one embodiment of the invention, the nano-porous permeable membrane of the present invention includes a plurality of pores having a diameter of 0.1 to 10 μm. Therefore, the nano-porous permeable membrane can store liquid by a capillary phenomenon. The solution may be a cell culture solution, a buffer solution, a cell-active substance in solution, or a cell protective substance in solution, and is preferably a cell culture solution. According to one embodiment of the invention, the nano-porous permeable membrane is capable of cell culture.

In the conductive polymer bio-electrode of the present invention, the PDMS device is located on the lowest layer; the nano-porous permeable membrane having a thickness similar to the depth of the intaglio groove is attached to the intaglio groove of the PDMS device to flatten the PDMS device and the nano-porous permeable membrane; the bio-signal transmission patterning is formed on the PDMS device and the nano-porous permeable membrane; and the uniform gold coating layer is located on the PDMS device, the nano-porous permeable membrane and the bio-signal transmission patterning. The bio-signal transmission patterning may be configured with a plurality of electrodes in accordance with the purpose of the bio-electrode. The gold coating layer is coated and manufactured on the PDMS device, the nano-porous permeable membrane, and the bio-signal transmission patterning, and thus, the conductivity of the conductive polymer bio-electrode is improved. According to one embodiment of the present invention, the gold coating layer is uniformly formed with a thickness of 0.1 to 10 μm on the PDMS device, the nano-porous permeable membrane and the bio-signal transmission patterning. If the thickness of the gold coating layer is 0.1 μm or less, the coating layer may not be easily formed, and the coating layer may be peeled off by even small impact to degrade the conductivity. If the thickness of the gold coating layer exceeds 10 μm, the coating layer may be destroyed by mechanical deformation, and the pores of the nano-porous permeable membrane are blocked, so that the surface area may be be reduced.

According to another aspect of the invention, the present invention provides a method of manufacturing a conductive polymer bio-electrode including the following steps:
(a) a first step of manufacturing a 3D substrate for a PDMS device including an intaglio groove for attaching a nano-porous permeable membrane;
(b) a second step of manufacturing a PDMS device including the intaglio groove for attaching the nano-porous permeable membrane by using the 3D substrate;
(c) a third step of manufacturing the nano-porous permeable membrane by using electrospinning;
(d) attaching the nano-porous permeable membrane to the intaglio groove formed in the PDMS device by using a PDMS solution;
(e) a fifth step of performing bio-signal transmission patterning on the PDMS device to which the nano-porous permeable membrane is attached; and
(f) a sixth step of performing gold coating on the PDMS device on which the bio-signal transmission patterning is performed.

First Step: Manufacturing of 3D Substrate for PDMS Device Including Intaglio Groove for Attaching Nano-Porous Permeable Membrane According to one embodiment of the present invention, the 3D substrate for the PDMS device of the present invention may be manufactured according to the following steps:
(a) designing a 3D substrate for manufacturing the PDMS device having a thickness of 250 to 350 μm and having an intaglio groove having a depth of 100 to 200 μm to which the nano-porous permeable membrane for cell culture can be attached;
(b) manufacturing the 3D substrate for the PDMS device by manufacturing a 3D printing ink by mixing a UV curable plastic and a dissoluble support wax, and after that, stacking the 3D printing ink by using a 3D printer;
(c) loading the 3D substrate for the PDMS device in an oven of 60 to 80° C. for 0.5 to 2 hours to dissolve the support wax;
(d) immersing the 3D substrate for the PDMS device in which the support wax is dissolved in cooking oil of 50 to 70° C. and, after that, performing ultrasonic cleaning;

(e) cleaning the 3D substrate for the PDMS device subjected to the ultrasonic cleaning by immersion in an EZ rinse solution for 5 to 20 minutes; and (f) cleaning the 3D substrate for the PDMS device cleaned with the EZ rinse solution with distilled water and, after that, performing drying.

According to an embodiment of the present invention, in step (c), if the support wax in the 3D substrate for the PDMS device is dissolved in the oven of less than 60° C., there is a disadvantage in that the dissolution time is increased, and if the support wax in the 3D substrate for the PDMS device is dissolved in the oven of more than 80° C., there is a disadvantage in that the support wax is burned and stain occurs on the substrate.

According to another embodiment of the present invention, in step (d), if the 3D substrate for the PDMS device is immersed in the cooking oil of less than 50° C. and, after that, the ultrasonic cleaning is performed, it takes more time to remove the dissolved support wax, and even if the 3D substrate for the PDMS device is immersed in the cooking oil of more than 70° C. and, after that, the ultrasonic cleaning is performed, the efficiency of removal of the dissolved support wax is not improved.

Second Step: Manufacturing of PDMS Device Including Intaglio Groove for Attaching Nano-Porous Permeable Membrane According to one embodiment of the present invention, the PDMS device of the present invention can be manufactured according to the following steps:

(a) manufacturing a PDMS reaction solution by mixing the PDMS solution and a curing agent in a weight ratio of 10:0.5 to 10:2 (PDMS solution: curing agent) and removing bubbles by using a desiccator;

(b) manufacturing the PDMS device by applying the PDMS reaction solution to the dried 3D substrate for the PDMS device and performing heat treatment in an oven of 40 to 50° C. for 22 to 26 hours; and (c) removing the PDMS device from the 3D substrate.

According to an embodiment of the present invention, if the PDMS solution and the curing agent are mixed at a weight ratio of less than 10:0.5 (PDMS solution:curing agent), the curing time is further taken for the 3D substrate for the PDMS device, and if the PDMS solution and the curing agent are mixed at a weight ratio of more than 10:2 (PDMS solution:curing agent), it is difficult to remove bubbles by using the desiccator.

According to another embodiment of the present invention, if the PDMS reaction solution is applied to the 3D substrate for the PDMS device and heat treatment is performed in an oven of less than 40° C., it takes more curing time, and even if the PDMS reaction solution is applied to the 3D substrate for the PDMS device and the heat treatment is performed in an oven of more than 50° C., the curing time is the same.

Third Step: Manufacturing of Nano-Porous Permeable Membrane by Using Electrospinning According to one embodiment of the invention, the nano-porous permeable membrane of the present invention is manufactured by the electrospinning method through the following steps:

(a) manufacturing a polyurethane electrospinning solution by adding 10 to 20 parts by weight of polyurethane to 100 parts by weight of a dimethylformamide solution and performing mixing for 22 to 26 hours; and (b) manufacturing the nano-porous permeable membrane having a thickness of 150 to 250 μm by spinning a total of 4 to 6 ml of the polyurethane electrospinning solution under conditions of a voltage of 10 to 20 kV, a spinning rate of 0.05 to 0.3 ml/h, a needle diameter of 20 to 30 G, and a spinning distance of 20 to 40 cm and in an atmosphere of a humidity of 20 to 40% and a temperature of 25 to 35° C.

The diameter of the nano-fiber manufactured by the electrospinning highly depends on the spinning conditions. In particular, the viscosity of the electrospinning solution is the largest determination factor, and thus, if the viscosity of the solution is high, coarse fibers can be manufactured. In general, the diameter of the nano-fibers is proportional to the square of the concentration of the electrospinning solution. When the nano-fibers are stacked to form a fibrous membrane, pores caused by gaps between the fibers are formed. Since the size of the pore is proportional to the diameter of the nano-fiber, the smaller the diameter of the nano-fiber, the smaller the gap between the fibers. Therefore, if the pores are formed to be smaller and the diameter of the nano-fiber becomes larger, the gap between the fibers becomes larger, so that the pore having a large diameter is formed. The pores relate to the ability to flow across the membrane, and the degree of storage of the solution depends on the size of the pores.

According to one embodiment of the present invention, if less than 10 parts by weight of the polyurethane is added to 100 parts by weight of the dimethylformamide solution and mixing is performed to manufacture an electrospinning solution, the viscosity of the pinning solution is low, and thus, the nano-fibers having a small diameter are formed. The jet may be spun onto the granular shape rather than the fiber shape, and thus, nano-pores may not be formed. In addition, if if more than 20 parts by weight of the polyurethane is added to 100 parts by weight of the dimethylformamide solution and mixing is performed to manufacture an electrospinning solution, the viscosity of the spinning solution is too high, and thus, the nano-fibers having a large diameter are spun, and the number of pores formed per unit area becomes smaller and the size of the pores becomes larger, so that there is a disadvantage in that the amount of solution that can be stored is reduced.

According to another embodiment of the present invention, in the electrospinning, a total of 4 to 6 ml of the polyurethane electrospinning solution is spun under conditions of a voltage of 10 to 20 kV, a spinning rate of 0.05 to 0.3 ml/h, a needle diameter of 20 to 30 G, and a spinning distance 20 to 40 cm and in an atmosphere of a humidity of 20 to 40% and a temperature of 25 to 35° C. Preferably, in the electrospinning, a total of 5 ml of the polyurethane electrospinning solution is spun under conditions of a voltage of 15 kV, a spinning rate of 0.1 ml/h, a needle diameter of 25 G, and a spinning distance of 30 cm and in an atmosphere of a humidity of 30 and a temperature of 30° C. These conditions are the best electrospinning conditions for manufacturing the nano-porous permeable membrane including a plurality of pores having a thickness of 150 to 250 μm and a diameter of 0.1 to 10 μm.

Fourth Step: Attaching Nano-Porous Permeable Membrane to PDMS Device

The nano-porous permeable membrane manufactured above is attached to the PDMS device manufactured in the above-described step. For this purpose, a PDMS solution is manufactured, and only a very small amount of the PDMS solution is applied to the intaglio groove of the PDMS device, and after that, the nano-porous permeable membrane is attached. When an excessive amount of the PDMS solution is used, the PDMS solution is absorbed and cured in the nano-porous permeable membrane by a capillary phenomenon, and thus, the pores of the permeable membrane disappear. Therefore, only a very small amount of the PDMS solution is used.

Fifth and Sixth Steps: Patterning and Gold Coating for Transmitting Bio-Signal

According to the exemplary embodiment of the present invention, an electrode is provided so that the electrical signal transmitted to the living body or the electrical signal transmitted from the living body can be moved by performing the bio-signal transmission patterning on the PDMS device to which the nano-porous permeable membrane is attached.

According to another embodiment of the present invention, after the bio-signal transmission patterning is completed, a gold coating layer is uniformly formed with a thickness of 0.1 to 10 μm on the PDMS device, the nano-porous permeable membrane, and the bio-signal transmission patterning. Since the gold coating layer is configured with gold (Au) having an excellent bio-compatibility and is uniformly formed with a thickness of 0.1 to 10 μm, the gold coating layer has an advantage of maintaining the conductivity without blocking pores of the nano-porous permeable membrane while improving the conductivity.

EXAMPLE

Example 1: Manufacturing of 3D Substrate for Manufacturing PDMS Device

Figure 2:
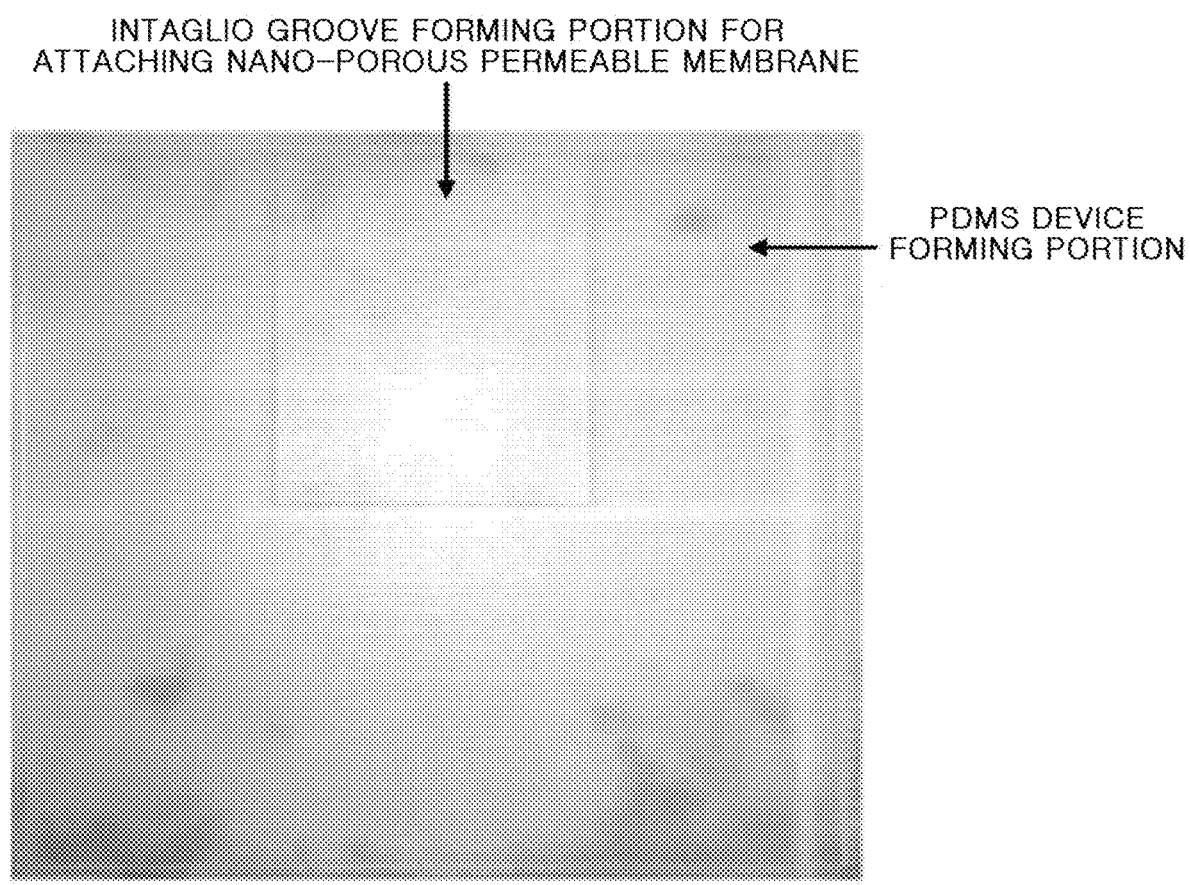
FIG. 2 illustrates the 3D substrate for the PDMS device including the intaglio groove for attaching the rectangular nano-porous permeable membrane manufactured by using 3D printing.

In order to manufacture the PDMS device, a 3D substrate for manufacturing the PDMS device were designed by using the Inventor (Autodesk, USA) program, a 3D design program (refer to FIG. 1). The overall appearance of the 3D substrate for manufacturing the PDMS device was designed in various forms such as a rectangle, a triangle, a circle, a pentagon. The 3D substrate for manufacturing the PDMS device is designed to include a PDMS device forming portion (embossed form) where the PDMS device is formed at the time of manufacturing the PDMS device by pouring the PDMS solution on the 3D substrate and an intaglio groove forming portion for attaching the permeable membrane having a predetermined size to which the polyurethane nano-porous permeable membrane is attached (refer to panel A of FIG. 1). In the 3D substrate for the PDMS device having a rectangular shape to which the polyurethane nano-porous permeable membrane of Panel A of FIG. 1 is attached, the PDMS device having a thickness of 250 to 350 μm and horizontal and vertical lengths of 5 cm may be formed, and the intaglio groove for attaching the nano-porous permeable membrane having a depth of 100 to 200 μm and horizontal and vertical lengths of 2 to 2.5 cm may be formed inside of the PDMS device. The 3D substrate for manufacturing the PDMS device was manufactured by using a 3D printer (PROJET 3510 HD) employing the photocurable principle, as a main material, VISIJET M3 crysta, which is a kind of ultraviolet (UV)-curable plastic was used, and as a support material, Support VISIJET S300 which is one of wax materials having melting and non-toxic properties was used. The 3D substrate for manufacturing the PDMS device was manufactured by stacking the VISIJET M3 crystal solution according to the design of Panel A of FIG. 1, culturing was performed for 1 hour in a laboratory oven at 70° C. to remove the Support VISIJET S300. The 3D substrate for manufacturing the PDMS device in which the Support VISIJET S300 was dissolved through the culturing was immersed in an ultrasonic cleaner filled with cooking oil of 60° C., and ultrasonic cleaning as a first cleaning process was performed for 1 hour. After that, the 3D substrate was immersed in the EZ Rinse solution, and cleaning as a second cleaning process was for 10 minutes. The 3D substrate for manufacturing the PDMS device for which the first and second cleaning processes were sequentially performed is subjected to the last third cleaning process using distilled water, and after, drying was performed. FIG. 2 illustrates the 3D substrate for manufacturing the PDMS device manufactured through the above-described method. The 3D substrate for manufacturing the PDMS device is configured with the PDMS device forming portion for forming the PDMS device, which is an intaglio portion, and the intaglio groove forming portion for attaching the nano-porous permeable membrane to which the polyurethane nano-porous permeable membrane is attached, which is an embossed portion.

Example 2: Manufacturing of PDMS Device

Figure 3:
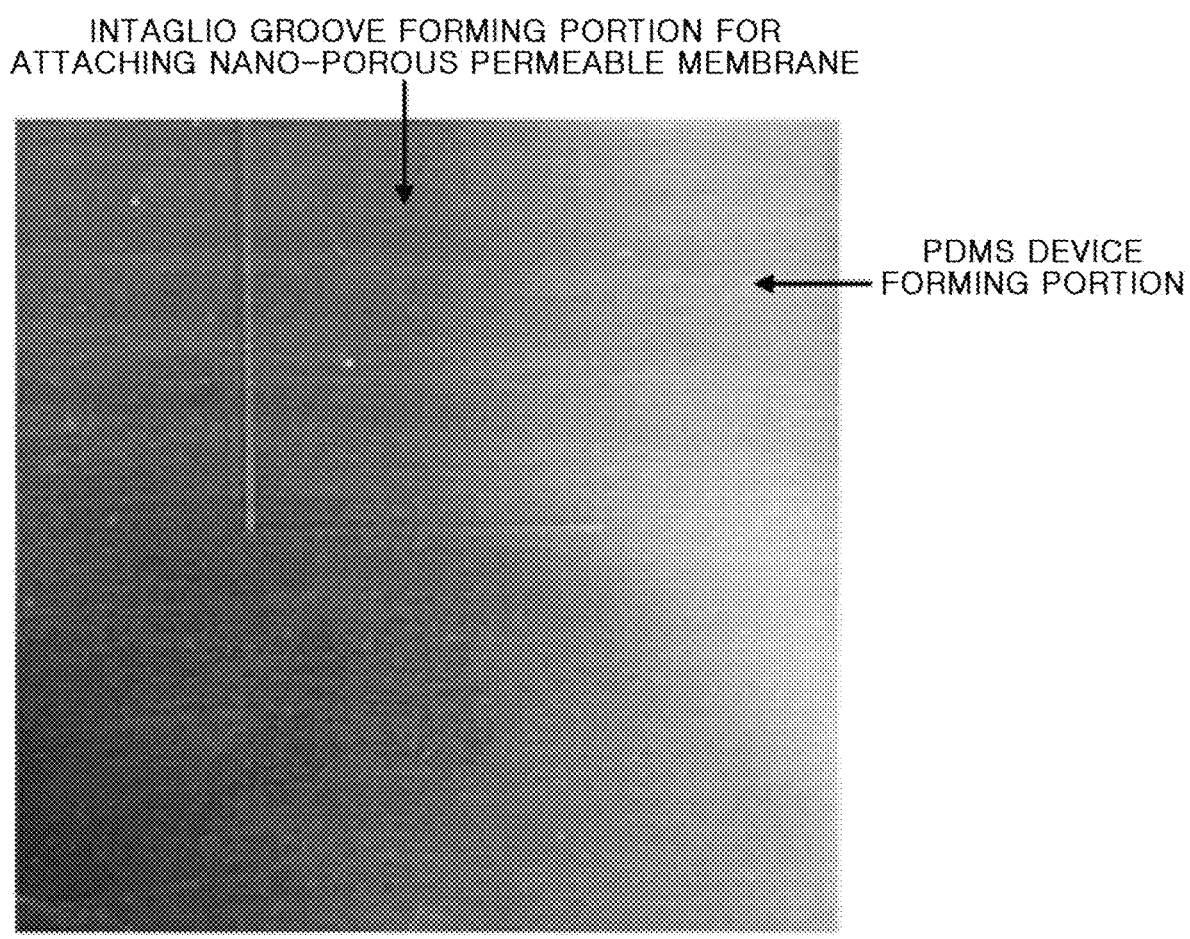
FIG. 3 illustrates the PDMS device including the intaglio groove for attaching the rectangular nano-porous permeable membrane manufactured by curing a PDMS solution in the 3D substrate for the PDMS device.

The PDMS reaction solution was manufactured in order to manufacture the PDMS device of the present invention. In the PDMS reaction solution, the PDMS solution and the curing agent were mixed at a ratio of 10:1, and after that, bubbles were sufficiently removed by using a desiccator. 3 ml of the PDMS reaction solution from which the bubbles were removed was applied to the manufactured 3D substrate for manufacturing the PDMS device, and after that, heat treatment was performed for 24 hours in a lavatory oven of 45° C., and curing was performed. The cured PDMS device was detached from the 3D substrate for manufacturing the PDMS device. FIG. 3 illustrates the PDMS device manufactured by the above-described method. The PDMS device is configured with the PDMS substrate portion and the intaglio groove for attaching the nano-porous permeable membrane to which the polyurethane nano-porous permeable membrane are attached. The PDMS device has a thickness of 250 to 350 μm and horizontal and vertical lengths of 5 cm. The intaglio groove for attaching the nano-porous permeable membrane existing inside the PDMS device has a depth of 100 to 200 μm and horizontal and vertical lengths of 2 to 2.5 cm.

Example 3: Manufacturing of Polyurethane Nano-Porous Permeable Membrane

In the present invention, a nano-fiber was attached to the PDMS device to manufacture a bio-electrode having improved conductivity and bio-compatibility. As the polymer material for manufacturing the nano-fiber, a polyurethane having an excellent bio-compatibility was selected, and a polyurethane nano-porous permeable membrane was manufactured by using an electrospinning method. For this purpose, 15 parts by weight of polyurethane was added to 100 parts by weight of dimethylformamide solution and mixed for 24 hours to manufacture a polyurethane electrospinning solution. Under the spinning conditions of a voltage of 15 kV, a spinning rate of 0.1 ml/h, a needle diameter of 25 G, a spinning distance of 30 cm and in the atmosphere of a temperature of 30° C. and a humidity of 30%, by electrospinning a total of 5 ml of polyurethane electrospinning solution, a polyurethane nano-porous permeable membrane was manufactured. The thickness of the polyurethane nano-porous permeable membrane manufactured under the electrospinning conditions was similar to the depth (100 to 200 μm) of the intaglio groove for attaching the nano-porous permeable membrane. The thickness (150 to 250 μm) of the polyurethane nano-porous permeable membrane is determined to be an appropriate thickness in consideration of the intaglio groove for attaching the nano-porous permeable membrane, and it is determined to be preferable that 5 ml polyurethane electrospinning solution under the above-described conditions is used to manufacture the permeable membrane having the thickness by the electrospinning.

Example 4: Attachment of Polyurethane Nano-Porous Permeable Membrane

Figure 4:
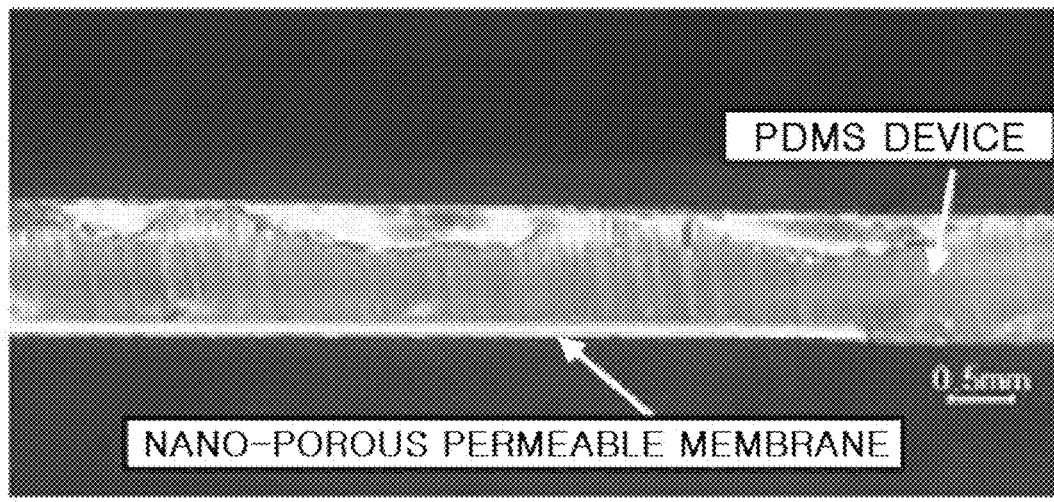
FIG. 4 illustrates an optical microscope images of the PDMS device attached with the nano-porous permeable membrane. Panel A illustrates a cross-sectional image of the PDMS device attached with the nano-porous permeable membrane taken by using a 10× optical microscope, and panel B illustrates a cross-sectional image of the PDMS device attached with the nano-porous permeable membrane taken by using a 50× optical microscope.
Figure 4:
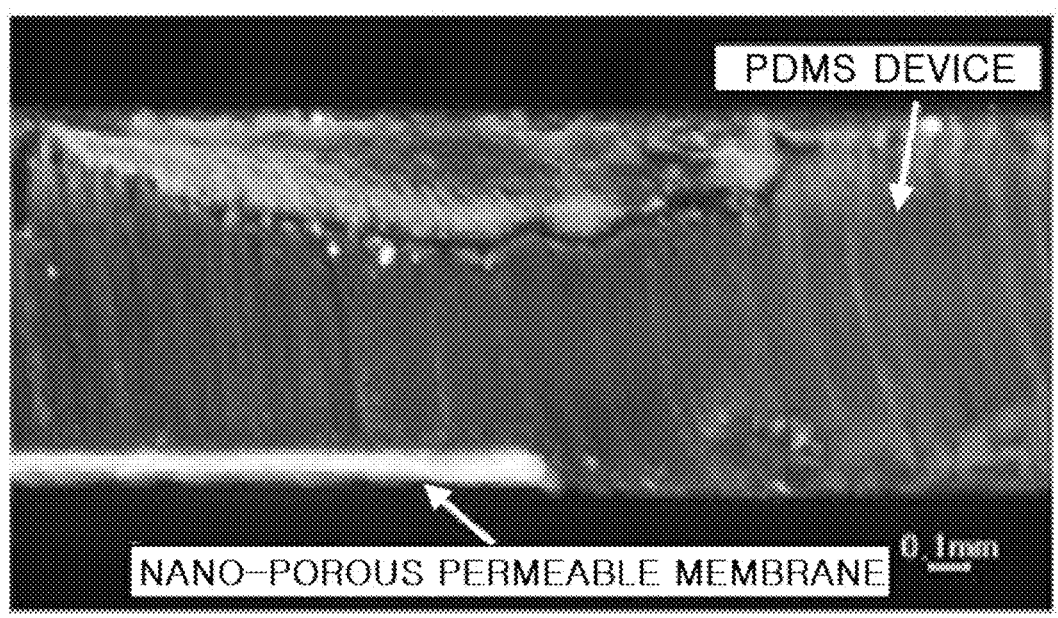
Figure 5:
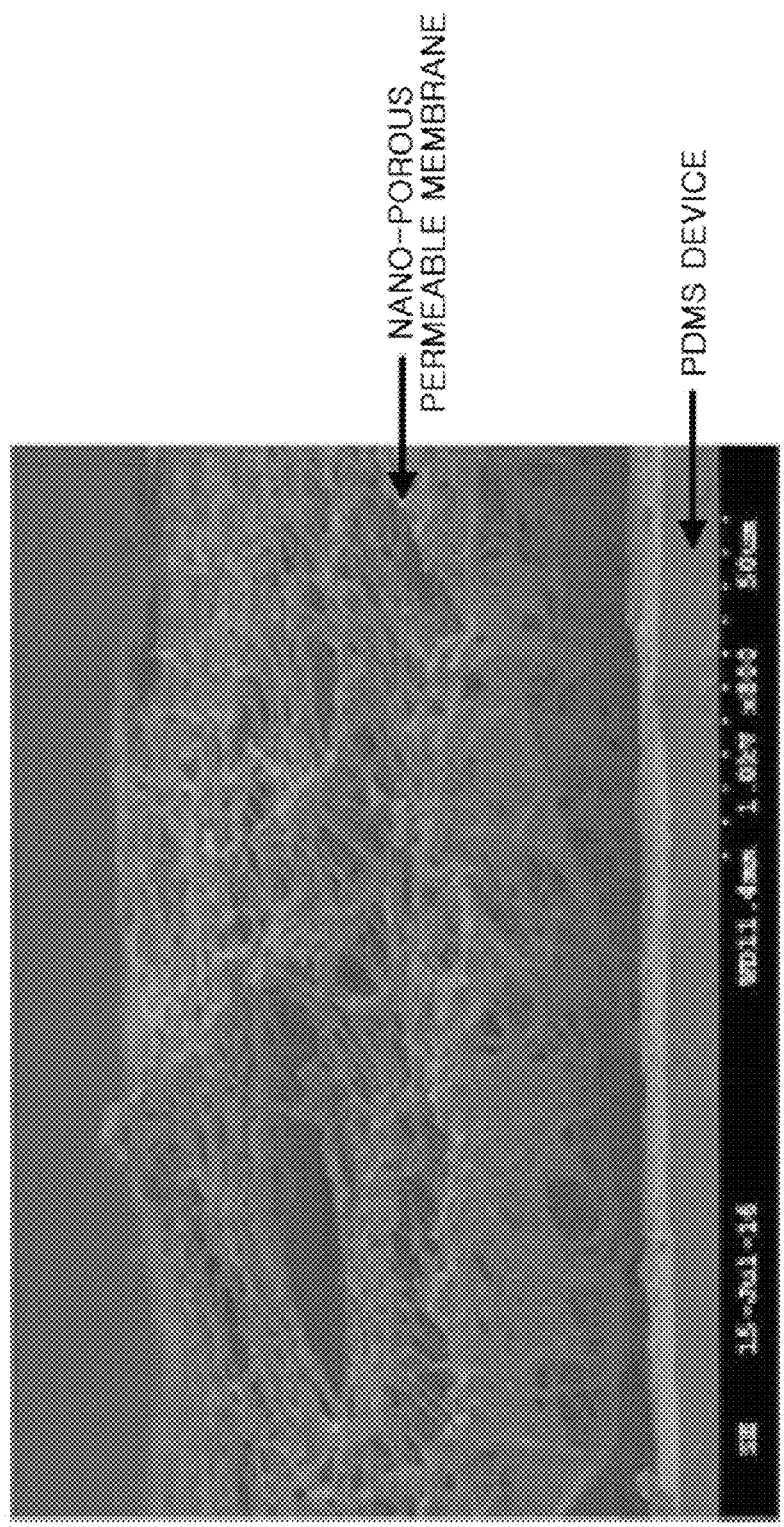
FIG. 5 illustrates an image of the nano-porous permeable membrane attached to the PDMS device by using a field emission scanning electron microscope (FESEM).

The manufactured polyurethane nano-porous permeable membrane was cut to have a length of 2 to 2.5 cm in horizontal and vertical lengths so as to fit the intaglio groove for attaching the nano-porous permeable membrane, and after that, the uncured pure PDMS solution was spread on the permeable membrane attachment portion, and the polyurethane nano-porous permeable membrane was attached thereon. The PDMS device attached with the polyurethane nano-porous permeable membrane (PU-PDMS device) was loaded into a 45° C. lavatory oven, and curing was performed for 1 hour. FIG. 4 illustrates optical microscope images of the PDMS device attached with the polyurethane nano-porous permeable membrane. As a result of the experiment, it can be confirmed that the polyurethane nano-porous permeable membrane with an appropriate thickness was attached to the PDMS device. At the time of attachment, if a large amount of pure, uncured PDMS solution is used, the PDMS solution is diffused into the pores of the permeable membrane and cured to fill the pores. Therefore, only such a small amount of PDMS solution that the PDMS solution was not diffused was applied. FIG. 5 illustrates an observation result of field emission scanning electron microscopy (FESEM) for the PDMS devices to which the polyurethane nano-porous permeable membrane is successfully attached. According to FIG. 5, in the PU-PDMS device, the PDMS solution is properly attached without diffusion into the polyurethane nano-porous permeable membrane, and thus, the porosity of the nano-porous permeable membrane was well maintained.

Example 5: Manufacturing of Conductive Polymer Bio-Electrode

Figure 6:
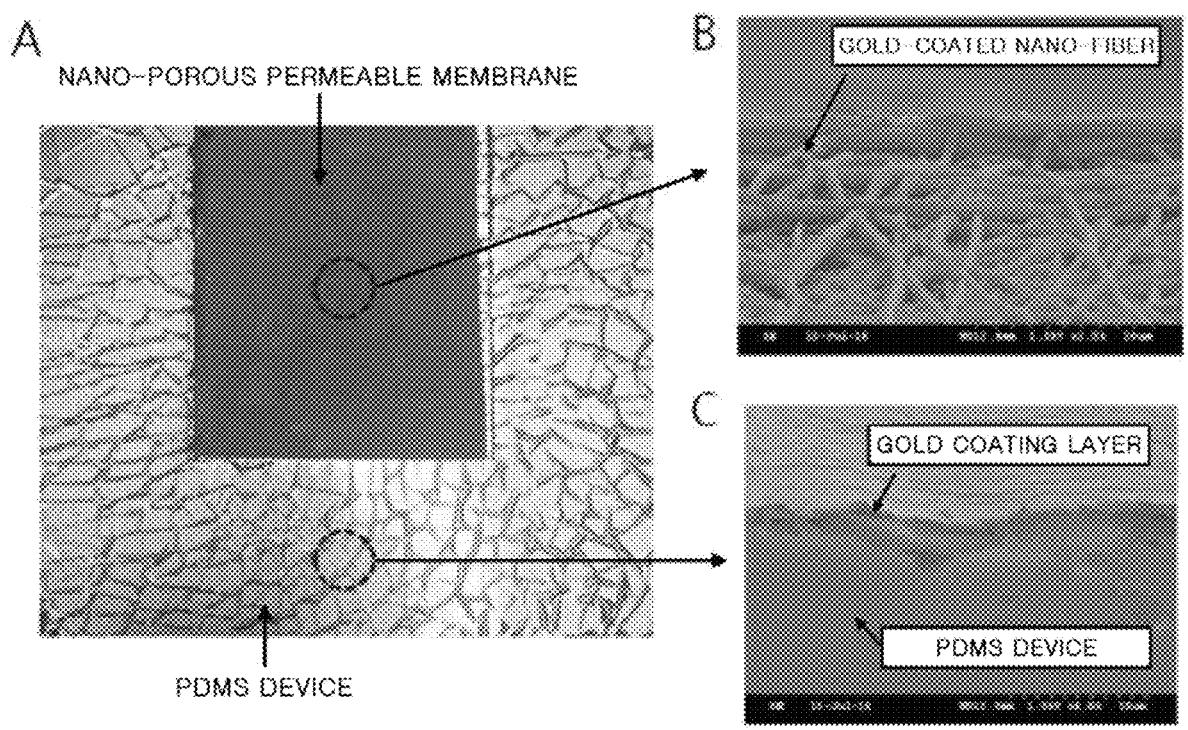
FIG. 6 illustrates a conductive polymer bio-electrode manufactured by performing gold coating on the PDMS device to which the nano-porous permeable membrane is attached. Panel A illustrates the conductive polymer bio-electrode; Panel B illustrates an image of the gold-coated nano-porous permeable membrane of the conductive polymer bio-electrode taken by using the FESEM; and Panel C illustrates an image of the gold-coated PDMS device of the conductive polymer bio-electrode taken by using the FESEM.

Gold (Au) coating was performed on the manufactured PU-PDMS device to manufacture a conductive polymer bio-electrode to which conductivity was added. Since gold is highly bio-compatible and non-toxic, the gold is safe for the human body. After performing the patterning to transmit the bio-signal, a conductive polymer bio-electrode capable of transmitting excellent signals was manufactured by coating gold with a thickness of 0.1 to 10 μm. Panel A of FIG. 6 illustrates the conductive polymer bio-electrode (gold-coated PU-PDMS device) of the present invention. It can be confirmed that, in the gold coating, the coating layer is thin and uniformly formed on the surface. Panel B of FIG. 6 illustrates a result of FESEM observation of the gold-coated polyurethane nano-porous permeable membrane of the conductive polymer bio-electrode. According to Panel B of FIG. 6, although the polyurethane nano-porous permeable membrane was coated with gold, the shape and porosity of the nano-fiber were well maintained. Panel C of FIG. 6 illustrates a result of FESEM observation of the PDMS device portion of the conductive polymer bio-electrode. It was confirmed that the PDMS device portion of the conductive polymer bio-electrode also was uniformly coated with gold like the PU nano-porous permeable membrane portion of the conductive polymer bio-electrode.

Experimental Example 1: Conductivity of Conductive Polymer Bio-Electrode

Figure 7:
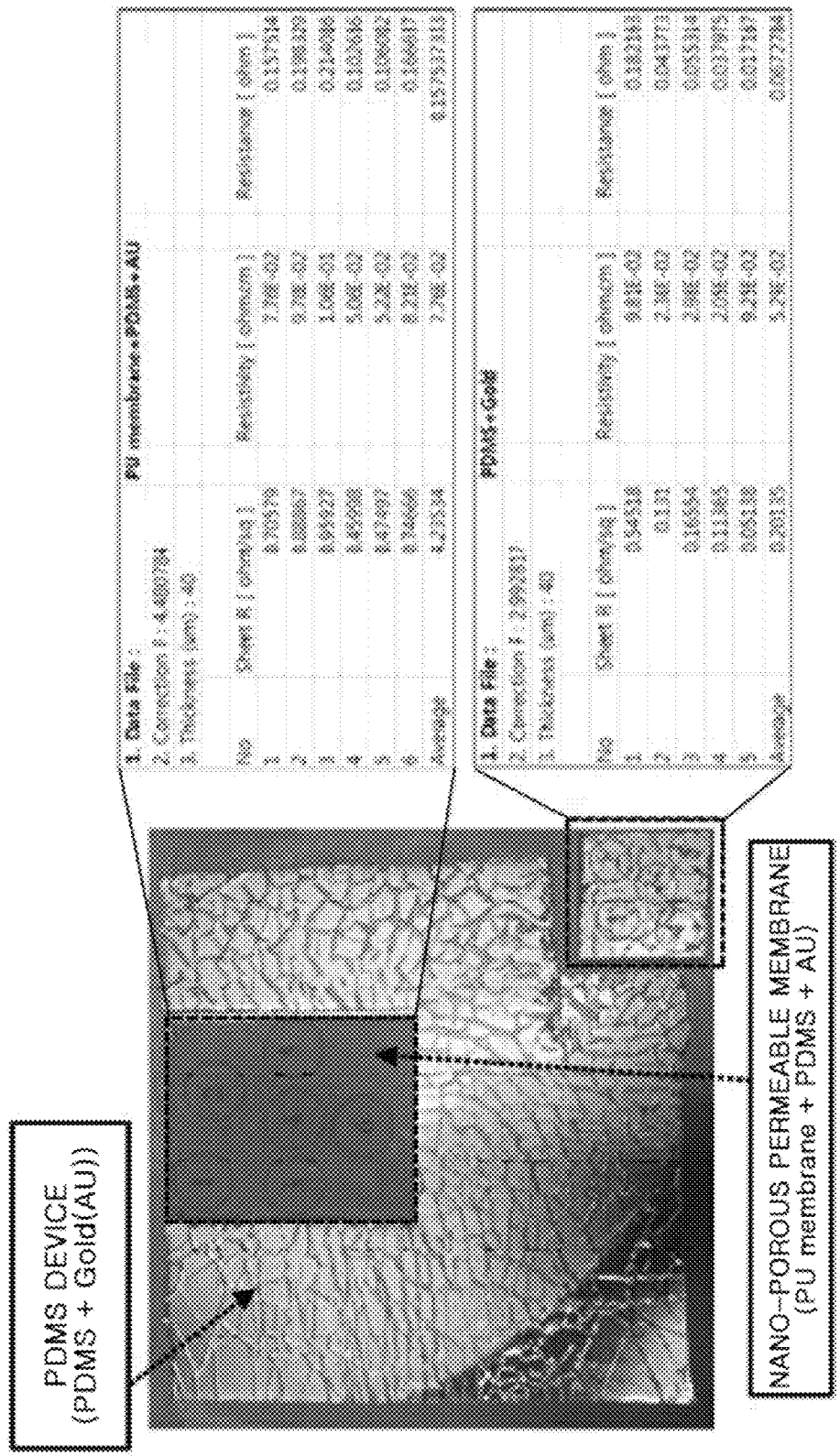
FIG. 7 illustrates results of measurement of surface specific resistance of the conductive polymer bio-electrode. After the measurement of the surface specific resistance of the gold-coated nano-porous permeable membrane and the gold-coated PDMS device is performed repeatedly five times, an average of the surface specific resistance was obtained.

In order to evaluate the conductivity of the conductive polymer bio-electrode of the present invention, the surface specific resistances of the nano-porous permeable membrane portion and the PDMS device portion were measured by using a surface resistance meter. FIG. 7 illustrates results of measurement of the surface specific resistances of the nano-porous permeable membrane portion and the PDMS device portion of the conductive polymer bio-electrode. In the case of the PU nano-porous permeable membrane, the specific resistance was measured at six different positions, and it was confirmed that the average specific resistance is 0.157 Ω; in the case of the PDMS device, the specific resistance was measured at five different positions, and it was confirmed that the average specific resistance is 0.067 Ω, so that it was confirmed to have excellent conductivity in all portions of the conductive polymer bio-electrode.

Figure 8:
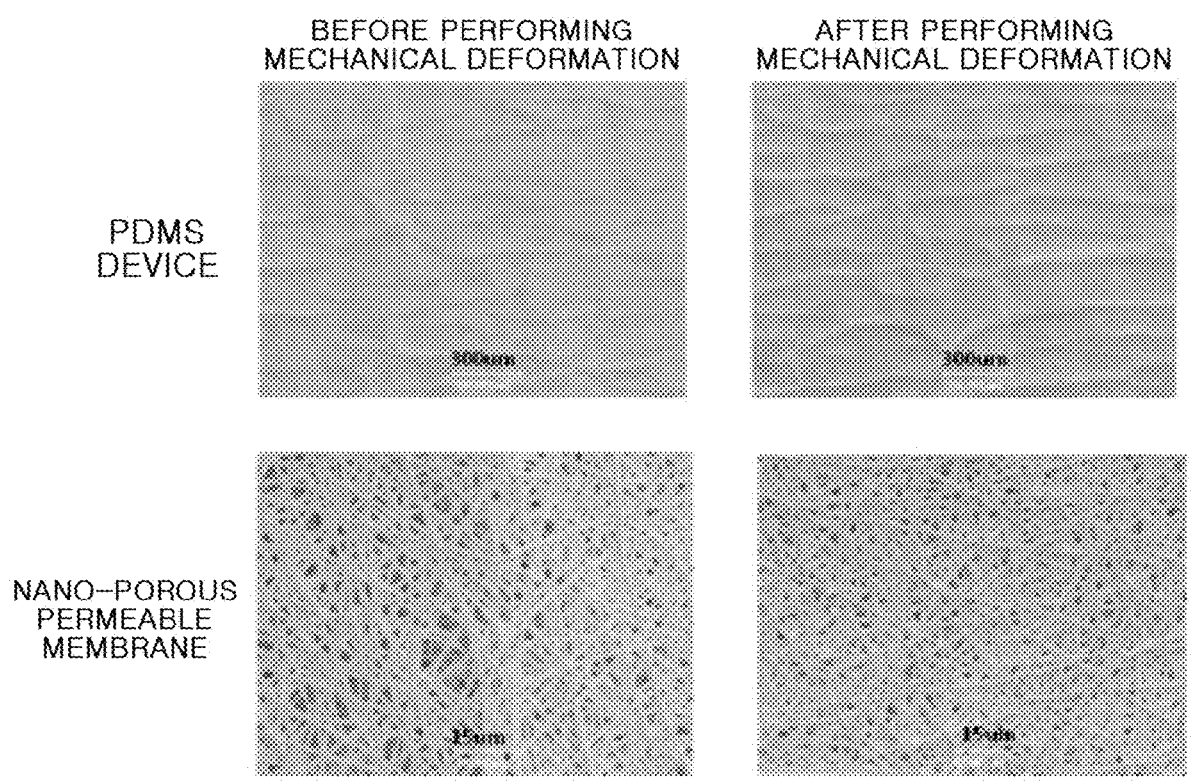
FIG. 8 illustrates results of physical change of the conductive polymer bio-electrode before and after performing mechanical deformation (bending) observed by using the FESEM. The bending was performed five times or more, and the gold-coated PDMS device and the nano-porous permeable membrane were imaged by the FESEM to observe the deformation of the gold coating, the change in shape of the nano-fiber, and the change of the pores.
Figure 9:
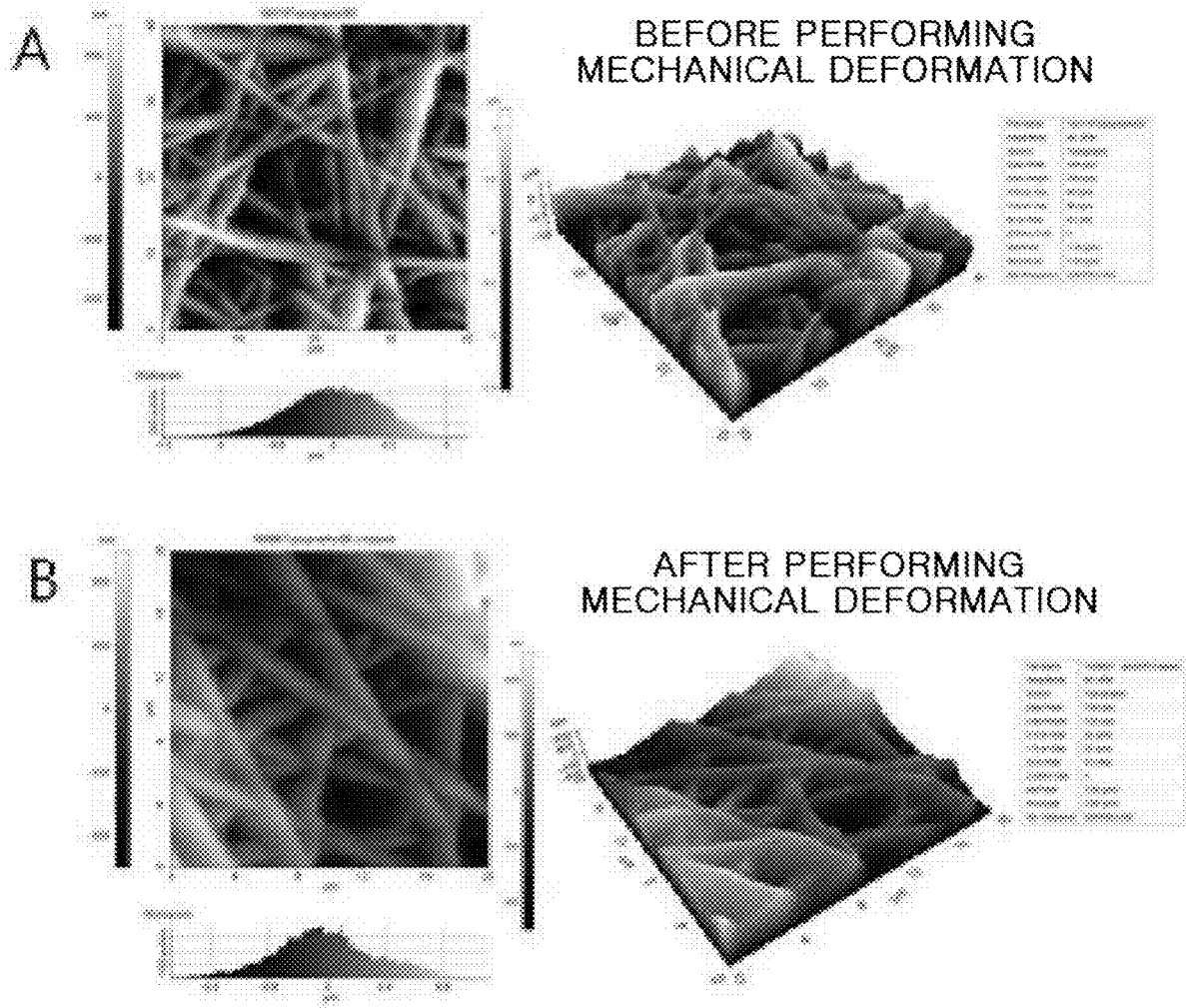
FIG. 9 illustrates results of physical changes of the conductive polymer bio-electrode before and after performing mechanical deformation observed by using an atomic force microscope (AFM). Panel A illustrates imaging results of the gold-coated nano-porous permeable membrane before mechanical deformation, and panel B illustrates imaging results of the gold-coated nano-porous permeable membrane after mechanical deformation.

Experimental Example 2: Durability to Physical Deformation of Conductive Polymer Bio-Electrode The bio-electrodes are introduced into the living body in various forms. Therefore, the bio-electrode inserted into the living body needs not to be changed in the gold coating state of the PDMS device, the porosity of the gold-coated permeable membrane, and the continuity of the nano-fiber even in the situation where a mechanical pressure is exerted. In order to confirm this, the surface of the conductive polymer bio-electrodes which were bent several times and the surface of the conductive polymer bio-electrodes which were not bent several times were observed by using an FESEM and an atomic force microscope (AFM). FIG. 8 illustrates results of observation of the surface state of the conductive polymer bio-electrode without bending (mechanical deformation) and the surface state of the conductive polymer bio-electrode after performing bending five to seven times by using the FESEM. As a result of the experiment, it was confirmed that there was no change in the shape and gold coating state of the nano-porous permeable membrane, and it was confirmed that there was also no change in the shape and gold coating state of the PDMS device portion. FIG. 9 illustrates the results of comparing and analyzing the surface state of the conductive polymer bio-electrode without bending and the surface state of the conductive polymer bio-electrode after performing bending several times by the AFM. Similarly to the result of the FESEM, it was confirmed that there was no change in the shape and the gold coating state of the nano-porous permeable membrane, and it was confirmed that there was also no change in the shape and gold coating state of the PDMS device portion.

Experimental Example 3: Durability of Conductive Polymer Bio-Electrode in Living Body Environment The human body consists of more than 70% water and maintains a constant temperature of 36.5° C. Therefore, in order to confirm the durability of the conductive polymer bio-electrode of the present invention to the living body environment, the bio-electrode was immersed in tertiary distilled water maintained at a temperature of 36.5° C., and after, the changes of the physical properties and conductivity of the electrode were confirmed with time.

Figure 10:
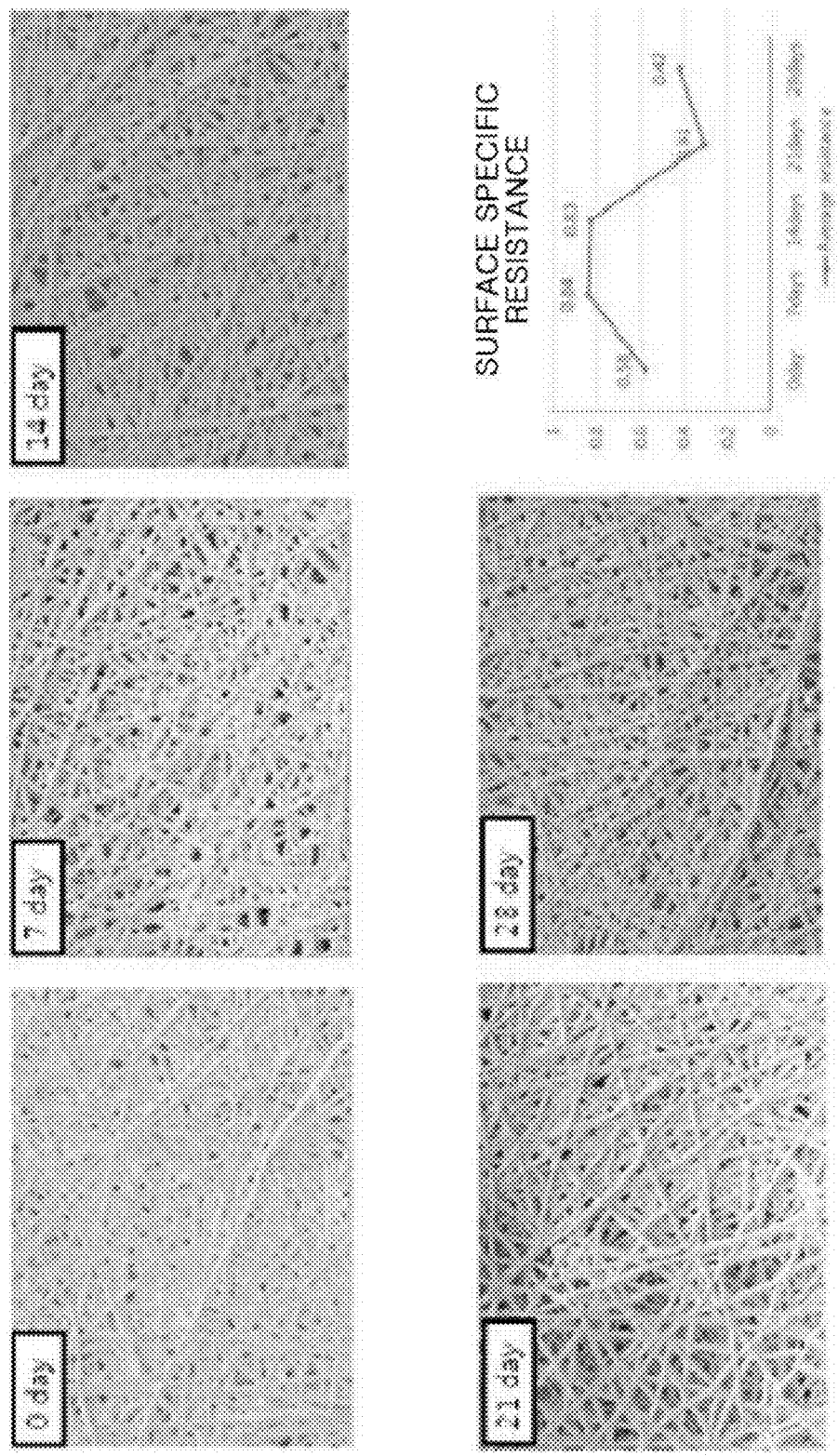
FIG. 10 is results of measurement obtained by immersing the conductive polymer bio-electrode in tertiary distilled water of 36.5° C. for 0, 7, 14, 21, and 28 days, and after that, observing the change of the nano-porous permeable membrane by using the FESEM to measure the surface specific resistance of the nano-permeable membrane.

FIG. 10 illustrates results of measurement obtained by immersing the conductive polymer bio-electrode of the present invention in tertiary distilled water maintained at a temperature of 36.5° C. for 7, 14, 21, and 28 days, and after that, imaging the shape of the nano-porous permeable membrane by using a scanning electron microscope (SEM). As a result of the experiment, it is confirmed that the nano-porous permeable membrane of the conductive polymer bio-electrode that was immersed in the tertiary distilled water for 28 days has no difference from the nano-porous permeable membrane that was not immersed in the tertiary distilled water in terms of the state of the gold coating layer, the shape of the nano-fiber, and the continuity of the nano-fiber.

In order to confirm that the conductivity of the conductive polymer bio-electrode is maintained under the living body conditions, the immersion was performed under the same conditions as described above, and the specific resistance of the surface was measured (refer to FIG. 10). As a result of the measurement, it was confirmed that the immersed conductive polymer bio-electrode had a resistance value of 0.31 to 0.84 Ω and an average resistance value of 0.59 Ω. Accordingly, despite being immersed in tertiary distilled water for 28 days at a temperature of 36.5° C., the conductive polymer bio-electrode had a resistance similar to the resistance of 0.58 Ω for 1 day, and thus, it was confirmed that the conductivity was maintained excellently in the living body conditions.

Experimental Example 4: Bio-Compatibility of Conductive Polymer Bio-Electrode

Figure 11:
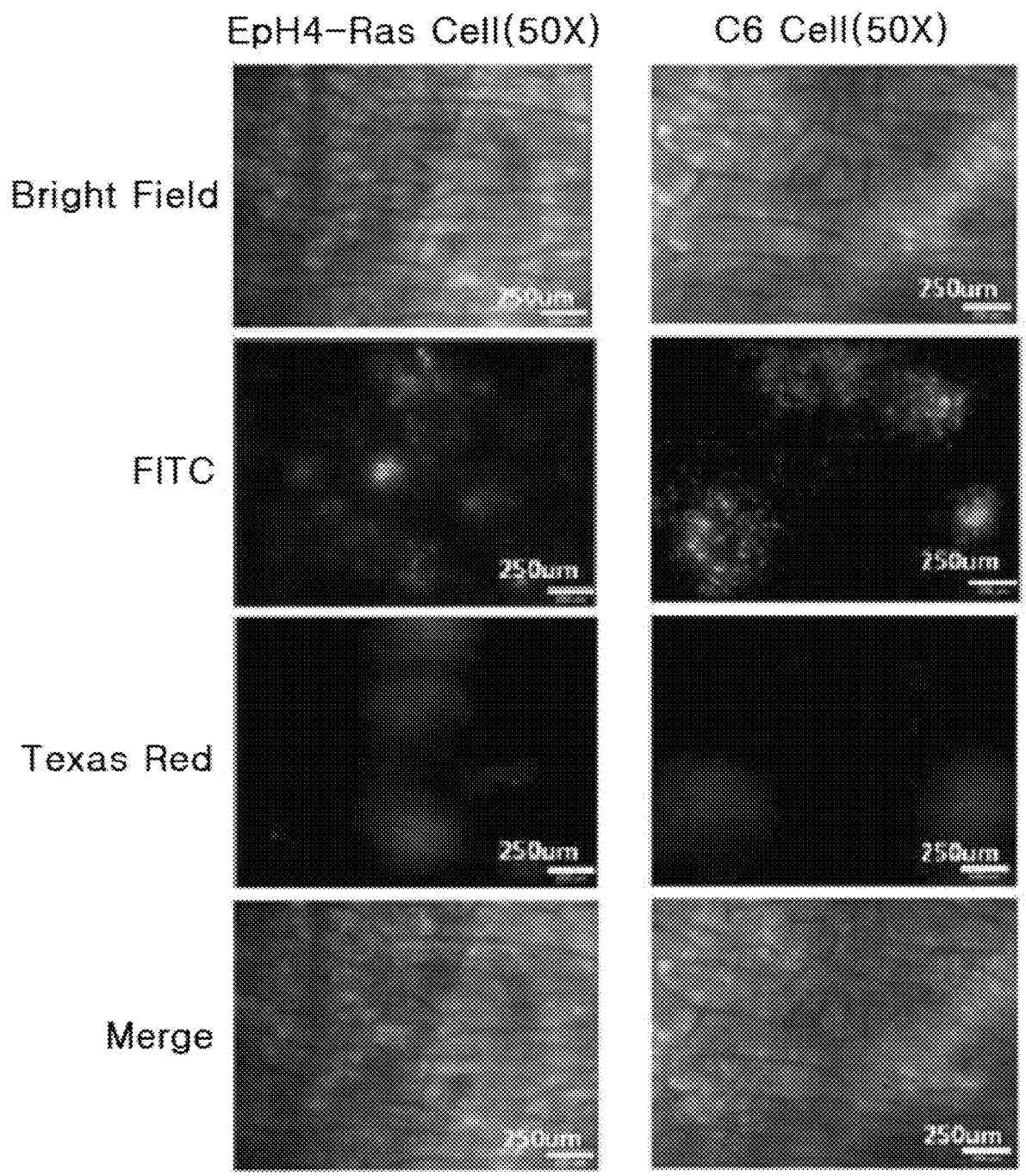
FIG. 11 illustrates results of observing the survival rate of cells by using a Live & Dead solution after culturing EpH4-Ras cells and C6 cells for 5 days in the nano-porous permeable membrane of the conductive bio-electrode.

In order to confirm the bio-compatibility of the conductive polymer bio-electrode, EpH4-Ras cells treated with Ras, which is a cancer gene, and the C6 cells which is one kind of fibroblasts were cultured for 5 days, on the epithelial cells of a rat on the nano-porous permeable membrane, treatment with a live/dead solution (The LIVE/DEAD® Cell Imaging Kit, Thermo Fisher Scientific) was performed, and a survival rate of the cells was confirmed (refer to FIG. 11). The live/dead solution can be used to distinguish between living cells maintaining cell membranes and dead cells that cannot maintain the cell membranes. After adding the live/dead solution to the cultured cells and observing by using a fluorescence microscope equipped with FITC and Texas RED filters, the living cells were stained with green fluorescence (FITC, ex/em=488 nm/515 nm), and dead cells were stained with red fluorescence (Texas RED, ex/em=570 nm/602 nm) by the exposed DNA due to disassembly of the nucleuses. As a result of the experiment, it was confirmed that the EpH4-Ras cells or C6 cells cultured on the nano-porous permeable membrane successfully survived, and thus, the number of living cells was larger than the number of dead cells (refer to FIG. 11). Therefore, it was confirmed that the conductive polymer bio-electrode of the present invention has excellent bio-compatibility to the extent that the conductive polymer bio-electrode is capable of cell culture.

Specific embodiments described in this specification are meant to represent preferred embodiments or examples of the present invention, and the scope of the present invention is not limited. It will be apparent to those skilled in the art that variations and other uses of the invention do not depart from the scope of the invention described in the claims.

INDUSTRIAL APPLICABILITY

The present invention relates to a bio-electrode for measuring a bio-signal on the basis of a nano-porous permeable membrane having a high specific surface area and a method of manufacturing the same, wherein the bio-electrode is expected to be able to replace a bio-electrode configured with a metal material by which the bio-signal transmission efficiency is degraded due to a high bio-incompatibility.

The invention claimed is:

1. A conductive polymer bio-electrode comprising;
    a polydimethylsiloxane (PDMS) device having an intaglio groove to which a nano-porous permeable membrane is to be attached and having a thickness of 250 to 350 µm;
    the nano-porous permeable membrane having a thickness of 50 to 200 µm which is to be attached to the intaglio groove of the PDMS device;
    a bio-signal transmission patterning formed on the PDMS device and the nano-porous permeable membrane; and
    a gold (Au) coating layer which is uniformly formed with a thickness of 0.1 to 10 µm on the PDMS device, the nano-porous permeable membrane, and the bio-signal transmission patterning.

2. The conductive polymer bio-electrode according to claim 1, wherein 25 to 50% of a total area of the PDMS device is an intaglio groove having a depth of 100 to 200 µm for attaching the nano-porous permeable membrane.

3. The conductive polymer bio-electrode according to claim 1, wherein the nano-porous permeable membrane is a permeable membrane having a thickness of 50 to 200 µm manufactured by electrospinning a bio-compatible polymer material and includes a plurality of pores having a diameter of 0.1 to 10 µm.

4. The conductive polymer bio-electrode according to claim 3, wherein the bio-compatible polymer material is any one or a mixture of two or more selected from a group consisting of polyurethane, polyacetal, polyamide, polyamide elastomer, polyester, polyester elastomer, polystyrene, polypropylene, polyacrylonitrile, polymethylmethacrylate, polyolefin, polysulfone, polyvinyl chloride, silicon, and polyethylene.

5. The conductive polymer bio-electrode according to claim 3, wherein the electrospinning is performed by spinning 4 to 6 ml of the electrospinning solution containing the bio-compatible polymer material under conditions of a voltage of 10 to 20 kV, a spinning rate of 0.05 to 0.3 ml/h, a needle diameter of 20 to 30 G, and a spinning distance of 20 to 40 cm in an atmosphere of a humidity of 20 to 40% and a temperature of 25 to 35° C.

6. The conductive polymer bio-electrode according to claim 1, wherein the nano-porous permeable membrane is capable of cell culture.

* * * * *